(12) United States Patent
Ries et al.

(10) Patent No.: US 7,647,111 B2
(45) Date of Patent: Jan. 12, 2010

(54) CONNECTOR ASSEMBLY FOR CONNECTING A LEAD AND AN IMPLANTABLE MEDICAL DEVICE

(75) Inventors: Andrew J. Ries, Lino Lakes, MN (US); Robert L. Olson, Vadnais Heights, MN (US); John E. Kast, Hugo, MN (US); Jeffrey J. Clayton, Ramsey, MN (US); Randy S. Roles, Crystal, MN (US)

(73) Assignee: Medtronic, Inc., Minneapolis, MN (US)

( * ) Notice: Subject to any disclaimer, the term of this patent is extended or adjusted under 35 U.S.C. 154(b) by 171 days.

(21) Appl. No.: 10/632,028

(22) Filed: Jul. 31, 2003

(65) Prior Publication Data

US 2005/0027326 A1 Feb. 3, 2005

(51) Int. Cl.
*A61N 1/375* (2006.01)
(52) U.S. Cl. ...................................................... 607/37
(58) Field of Classification Search ............ 607/37, 607/36; 439/909, 827, 335, 668
See application file for complete search history.

(56) References Cited

U.S. PATENT DOCUMENTS

| | | | |
|---|---|---|---|
| 4,105,037 A | 8/1978 | Richter et al. | |
| 4,445,511 A * | 5/1984 | Cowdery et al. | 607/37 |
| 4,655,462 A | 4/1987 | Balsells | |
| 4,848,346 A * | 7/1989 | Crawford | 607/37 |
| 4,934,366 A | 6/1990 | Truex et al. | |
| 4,934,367 A | 6/1990 | Daglow et al. | |
| 4,971,057 A | 11/1990 | Theres | |
| 5,076,270 A | 12/1991 | Stutz | |
| 5,252,090 A | 10/1993 | Giurtino et al. | |
| 5,261,395 A | 11/1993 | Oleen et al. | |
| 5,413,595 A * | 5/1995 | Stutz, Jr. | 607/37 |
| 5,514,172 A | 5/1996 | Mueller | |
| 5,545,188 A * | 8/1996 | Bradshaw et al. | 607/37 |
| 5,730,628 A * | 3/1998 | Hawkins | 439/843 |
| 5,769,671 A * | 6/1998 | Lim | 439/843 |

(Continued)

FOREIGN PATENT DOCUMENTS

EP 0 738 521 A1 10/1996

OTHER PUBLICATIONS

Merriam-Webster Online Dictionary, (http://www.webster.com); searched: flange.*

*Primary Examiner*—George R Evanisko
*Assistant Examiner*—Alyssa M Alter
(74) *Attorney, Agent, or Firm*—Michael C. Soldner (57) ABSTRACT

A connector assembly for detachably coupling a proximal end of a lead and an implantable medical device. The connector assembly includes a deflectable connector clip having a first arm, a second arm and a top portion extending between the first arm and the second arm. The first arm and the second arm detachably position the proximal end of the lead within the implantable medical device. A housing portion has a first deflection portion that deflects the connector clip from a first position corresponding to a first distance between the first arm and the second arm, to a second position corresponding to a second distance between the first arm and the second arm. Subsequent advancement of the lead through the first and second arms further deflects the connector clip from the second position to a third position, which transfers all of the spring force of the connector clip to the lead.

24 Claims, 8 Drawing Sheets

U.S. PATENT DOCUMENTS

| | | | |
|---|---|---|---|
| 5,807,144 A | 9/1998 | Sivard | |
| 5,931,861 A | 8/1999 | Werner et al. | 607/115 |
| 6,198,969 B1 * | 3/2001 | Kuzma | 607/37 |
| 6,245,103 B1 * | 6/2001 | Stinson | 623/1.22 |
| 2004/0093038 A1 * | 5/2004 | Biggs et al. | 607/37 |
| 2005/0027325 A1 * | 2/2005 | Lahti et al. | 607/37 |
| 2005/0027327 A1 * | 2/2005 | Ries et al. | 607/37 |

* cited by examiner

FIG. 14

CONNECTOR ASSEMBLY FOR CONNECTING A LEAD AND AN IMPLANTABLE MEDICAL DEVICE

CROSS-REFERENCE TO RELATED APPLICATIONS

Cross-reference is hereby made to commonly assigned related U.S. Applications, filed concurrently herewith, Ser. No. 10/632,026, entitled "CONNECTOR ASSEMBLY FOR CONNECTING A LEAD AND AN IMPLANTABLE MEDICAL DEVICE", Ser. No. 10/632,058, entitled "SMALL FORMAT CONNECTOR CLIP OF AN IMPLANTABLE MEDICAL DEVICE", and Ser. No. 10/632,027, entitled "ELECTRICAL CONNECTOR ASSEMBLY FOR COUPLING MEDICAL LEADS TO IMPLANTABLE MEDICAL DEVICES", incorporated herein by reference in their entirety.

FIELD OF THE INVENTION

The present invention relates to medical leads of implantable medical devices and, more particularly, to a connector assembly of an implantable medical device that facilitates coupling between a lead and circuitry of the implantable medical device.

BACKGROUND OF THE INVENTION

In the medical field, leads are used with a wide variety of medical devices. For example, leads are commonly implemented to form part of an implantable medical device (IMD), such as implantable cardiac pacemakers that provide therapeutic stimulation to the heart by delivering pacing, cardioversion or defibrillation pulses. The pulses can be delivered to the heart via electrodes disposed on the leads, e.g., typically near distal ends of the leads. In that case, the leads may position the electrodes with respect to various cardiac locations so that the pacemaker can deliver pulses to the appropriate locations. Leads are also used for sensing purposes, or both sensing and stimulation purposes.

In addition, leads are used in neurological devices such as deep-brain stimulation devices, and spinal cord stimulation devices. For example, the leads may be stereotactically probed into the brain to position electrodes for deep brain stimulation. Leads are also used with a wide variety of other medical devices including, for example, devices that provide muscular stimulation therapy, devices that sense chemical conditions in a patient's blood, and the like. In short, medical leads may be used for sensing purposes, stimulation purposes, or both.

An IMD typically includes one or more leads, a housing that houses circuitry of the IMD, and a connector block that couples the lead to the circuitry. In particular, the connector block includes electrical contact structures for coupling the lead to circuitry within the housing of the IMD so that therapeutic simulation can be provided through the lead, or sensed conditions can be recorded by the circuitry. One challenge in implementing medical leads in a medical device is the electrical coupling between a respective lead and circuitry of the IMD.

Various connection standards have been developed in order to ensure electrical connections between the IMD circuitry and the lead are acceptable, while also maintaining a sufficient hermetic seal between the connector block and the lead to avoid ingress of body fluids into the housing. These standards continue to evolve to accommodate new lead designs, such as in-line leads that include a plurality of electrical contact areas along axial positions of the lead.

In general, there remains a need for lead connector configurations that are simple to use and inexpensive to fabricate. Improved simplicity can help ensure that physicians can make the electrical connections during implantation of the IMD with minimal concern for electrical coupling malfunction. Reduced fabrication expense can help ensure that patient costs associated with an IMD can be minimized.

SUMMARY

In one embodiment, the invention provides an electrical connector clip for coupling a medical lead to circuitry of a medical device. The clip may comprise a first sidewall, a second sidewall, and an endwall attaching a first end of the first sidewall to a first end of the second sidewall such that the clip forms a substantially U-shaped configuration. A second end of the first side wall and a second end of the second sidewall may be spring biased toward one another. A protrusion may be formed on inner surfaces of each of the first and second side walls to facilitate electrical coupling to a medical lead upon positioning of the medical lead within the U-shape.

In another embodiment, the invention provides a connector block for an implantable medical device. The connector block may include a structure formed with a channel, the structure defining an access hole to the channel and a ridge formed in the access hole to provide a biasing mechanism for U-shaped electrical connector clip. The connector block may further include the substantially U-shaped electrical connector clip in the access hole to electrically couple to a medical lead upon insertion of the medical lead into the channel. The U-shaped electrical connector clip may be biased open by the ridge prior to the insertion of the medical lead.

In another embodiment, the invention provides an assembly that includes a structure formed with a channel, and a medical lead positioned in the channel. The structure may define an access hole to the channel and a ridge formed in the access hole. The assembly may further include a substantially U-shaped electrical connector clip in the access hole to electrically couple to the medical lead.

In another embodiment, the invention provides an implantable medical device. The implantable medical device may comprise a housing, circuitry within the housing and a connector block connected to the housing and including a structure formed with a channel, the structure defining an access hole to the channel and a spring bias ridge formed in the access hole. The implantable medical device may further include a medical lead in the channel, and a substantially U-shaped electrical connector clip in the access hole to electrically couple the medical lead to the circuitry.

In another embodiment, the invention provides a method that comprises inserting substantially U-shaped electrical connectors into holes of a lead connecting structure such that the U-shaped electrical connectors are biased open by ridges formed in the holes of the structure, and inserting a medical lead through a channel of the structure such that the lead passes through the U-shaped electrical connectors making electrical contact between the medical lead and the U-shaped electrical connectors.

The invention may be capable of providing a number of advantages. For example, the invention may improve and simplify electrical connections between implantable leads and circuitry of an implantable medical device. In particular, the invention may find useful application in in-line medical lead systems that use leads having multiple electrical contacts along axial positions of the respective leads. In that case, the invention may reduce size constraints of electrical contacts in an IMD, allowing electrical contact areas to be positioned on the lead in closer spatial proximity.

In addition, the invention may improve medical procedures, allowing physicians to make the electrical connections during implantation if the IMD with minimal concern for electrical coupling malfunction. The invention may also reduce costs associated with IMD fabrication, which can help minimize patient costs associated with an IMD.

Additional details of various embodiments are set forth in the accompanying drawings and the description below. Other features, objects and advantages will become apparent from the description and drawings, and from the claims.

BRIEF DESCRIPTION OF DRAWINGS

Advantages and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1:
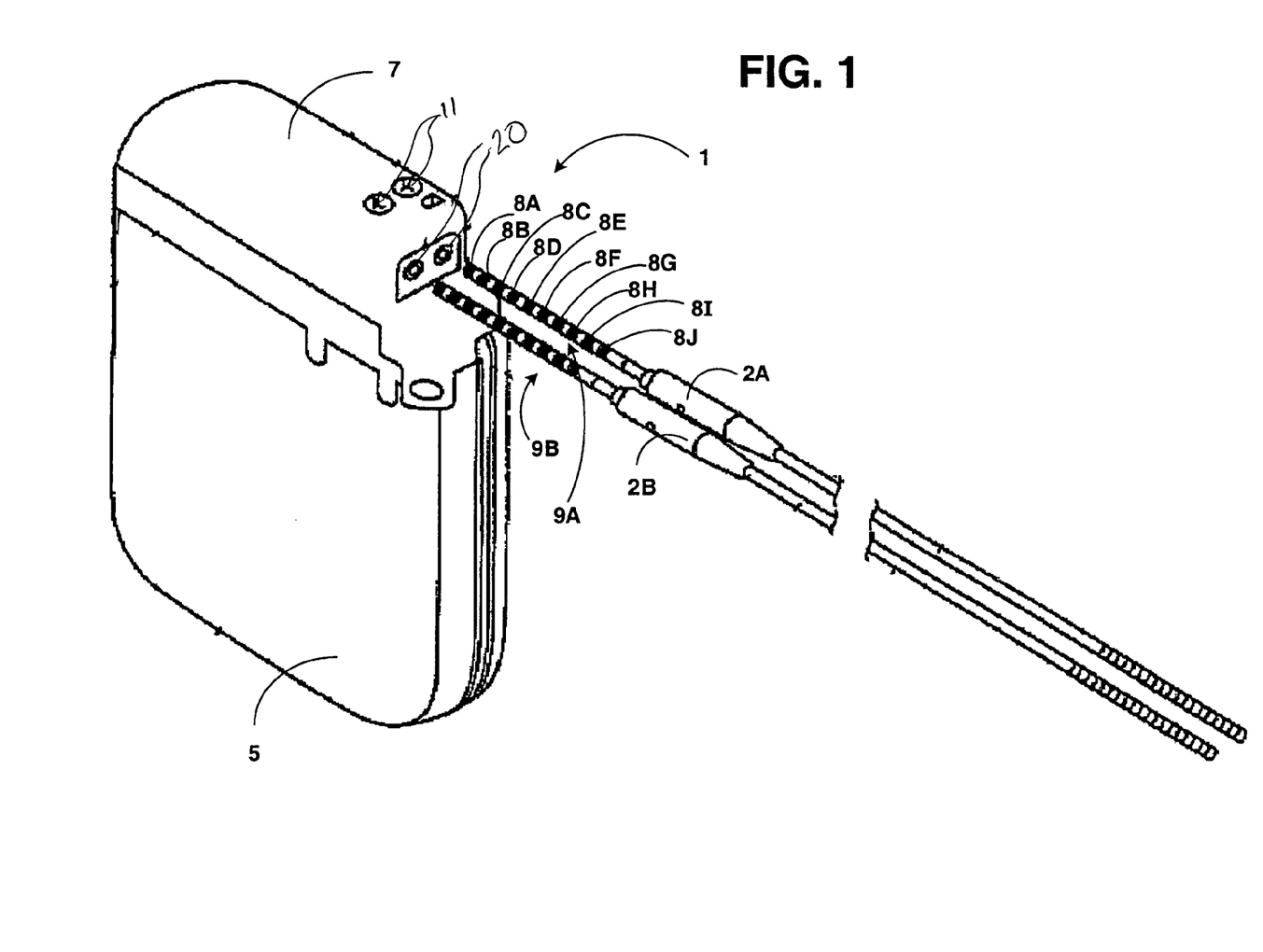
FIG. 1 is a perspective view of an exemplary implantable medical device capable of incorporating a connector assembly according to the present invention.

The present invention is directed to an electrical connector assembly for facilitating electrical connection between a medical lead and circuitry of an implantable medical device (IMD), and implantable medical devices employing such a connector assembly. For example, an improved connector clip that forms a conductive interface between a medical lead and IMD circuitry is described. Various components that assemble with the connector clip to form at least a portion of a connector block of an IMD are also described. FIG. 1 is a perspective view of an exemplary implantable medical device capable of incorporating a connector assembly according to the present invention. As illustrated in FIG. 1, an exemplary implantable medical device (IMD) 1 incorporating a connectory assembly according to the present invention includes a hermetically sealed, biologically inert housing 5, or "can", that houses IMD circuitry, one or more leads 2A, 2B that can be implanted in a patient, and a connector block 7 that receives proximal ends 9A, 9B of leads 2 to couple leads 2 to the circuitry in housing 5 as leads 2 are inserted within a connector port 20 formed in connector block 7. Once fully inserted within connector block 7, leads 2 are fixedly positioned within connector block 7 by tightening positioning screws 11 against leads 2.

As illustrated in FIG. 1, the proximal ends 9A and 9B of lead 2A and 2B include a plurality of electrical contact areas 8A-8J (collectively contact areas 8). The present invention facilitates electrical coupling to one or more of contact areas 8 within connector block 7. Moreover, the present invention improves such contact for inline configurations like FIG. 1 in which a plurality of electrical contact areas 8 are positioned axially along a length of leads 2. In particular, the present invention allows size reductions of contact areas 8 by improving electrical coupling clips, described below, that electrically interface with contact areas 8 inside connector block 7.

IMD 1 corresponds to any medical device that includes medical leads and circuitry coupled to the medical leads. By way of example, IMD 1 takes the form of an implantable cardiac pacemaker that provides therapeutic stimulation to the heart. Alternatively, IMD 1 may take the form of an implantable cardioverter or an implantable defibrillator, or an implantable cardiac pacemaker-cardioverter-defibrillator. IMD 1 may deliver pacing, cardioversion or defibrillation pulses to a patient via electrodes disposed on distal ends of leads 2. In other words, leads 2 position electrodes with respect to various cardiac locations so that IMD 1 can deliver pulses to the appropriate locations.

Alternatively, IMD 1 corresponds to a patient monitoring device, or a device that integrates monitoring and stimulation features. In those cases, leads 2 include sensors positioned along distal ends of the respective lead for sensing patient conditions. The sensors include, for example, electrical sensors, electrochemical sensors, pressure sensors, flow sensors, acoustic sensors, optical sensors, or the like. In many cases, IMD 1 performs both sensing and stimulation functions.

In still other applications, IMD 1 corresponds to a neurological device such as a deep-brain stimulation device or a spinal cord stimulation device. In those cases, leads 2 are stereotactically probed into the brain to position electrodes for deep brain stimulation, or into the spine for spinal stimulation. In other applications, IMD 1 provides muscular stimulation therapy, blood sensing functions, and the like. In short, IMD 1 corresponds to any of a wide variety of medical devices that implement leads and circuitry coupled to the leads.

As outlined in detail below, connector block 7 of the present invention incorporates various components that improve and simplify electrical coupling between leads 2 and circuitry in housing 5. More specifically, an electrical connector clip provides a conductive interface between a medical lead and IMD circuitry. In addition, various components that assemble with the connector clip to form at least a portion of connector block 7 of IMD 1 are also described. For example, an improved structure having a channel for mating with one or more of leads 2 is designed for use with the connector clip so that biasing of the connector clip can be achieved prior to insertion of one or more leads 2 into the channel. As described below, such biasing allows for ease of insertion of one or more of leads 2 into the channel of the structure that forms at least part of connector block 7. In other words, the connector clip defines a desired amount of insertion force for lead pins inserted into connector block 7.

Figure 2:
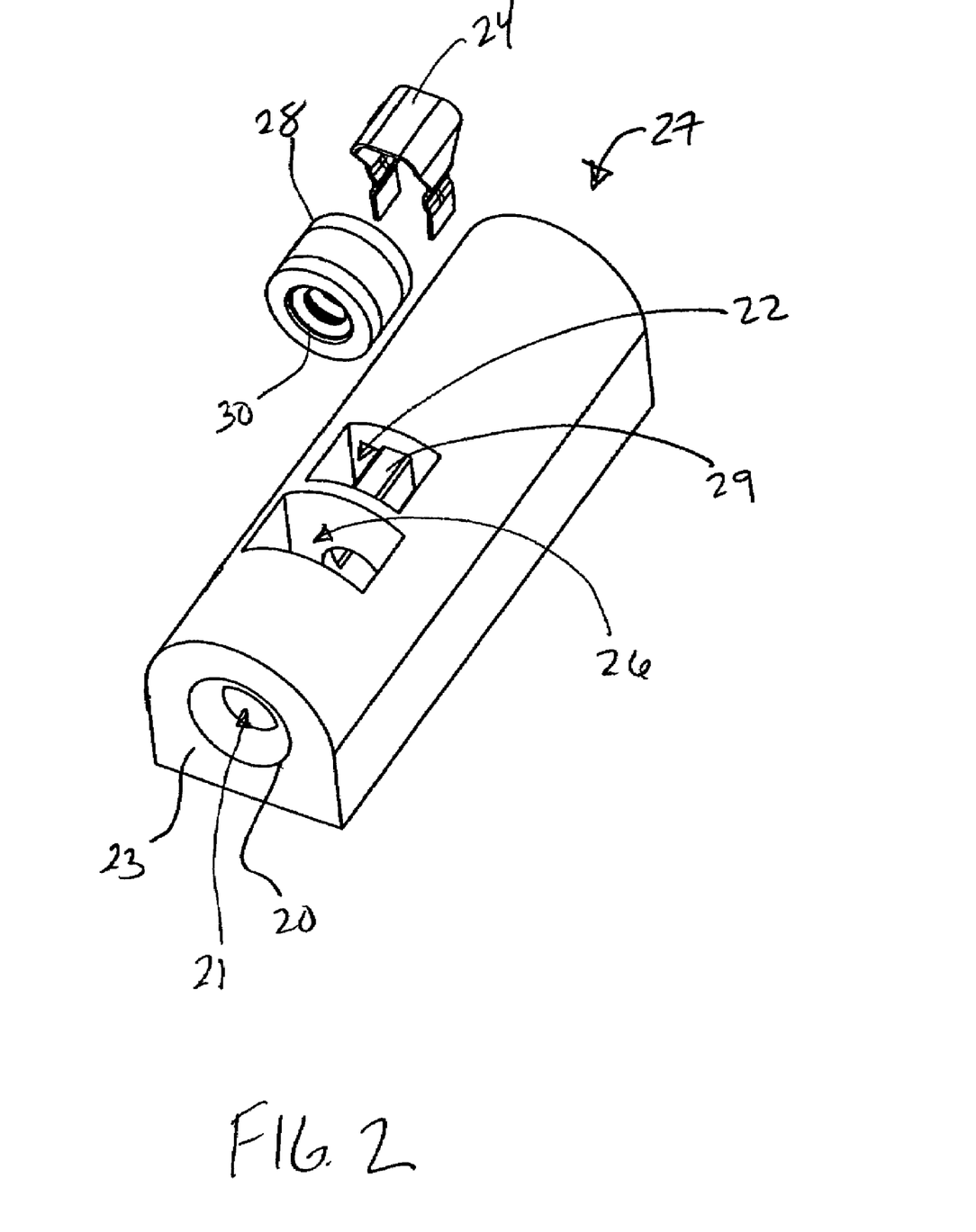
FIG. 2 is an exploded perspective view of components of a connector assembly of an implantable medical device according to the present invention.

FIG. 2 is an exploded perspective view of components of a connector assembly of an implantable medical device according to the present invention. In particular, according to the present invention a portion 27 of connector block 7 includes connector port 20, formed along a front end 23 of connector block 7 that is in fluid communication with a channel 21 formed therein for receiving a medical lead. Channel 21 extends from connector port 20 to a back end 25 (FIGS. 3 and 4), so that leads 2 are received within channel 21 of connector block 7 when inserted within connector port 20. A connector clip aperture 22 is formed along portion 27 of connector block 7 for insertably receiving an electrical connector clip 24. Aperture 22 provides side access to channel 21 for insertion of connector clip 24, and is sized to receive and position electrical connector clip 24 within connector block 7 so that electrical connector clip 24 electrically interfaces with contact areas 8 of leads 2 when leads 2 are inserted within channel 21 via connector port 20. In addition, a fluid sealing aperture 26 is formed along portion 27 of connector block 7 for insertably receiving a fluid seal 28. Similar to aperture 22, aperture 26 provides side access to channel 21 for insertion of fluid seal 28, and is sized to receive and position fluid seal 28 within connector block 7. Fluid seal 28 is generally cylindrical in shape and forms a through hole 30 for sealably receiving a medical lead inserted within channel 21 via connector port 20 of connector block 7 when seal 28 is inserted within aperture 26.

In operation, one or more of proximal ends 9A and 9B of leads 2 are inserted within channel 21 via connector port 20 and advanced through fluid seal 28 inserted within sealing hole 26. Fluid seal 28 is deformable and exerts sealing force against the circumference of proximal ends 9A and 9B of leads 2 between contact areas 8 to provide a fluid seal around leads 2. Proximal ends 9A, 9B extend into channel 21 so that contact areas 8 are brought into alignment with connector clip 24, which creates an electrical interconnection between contact areas 8 and circuitry within connector block 7.

Figure 7:
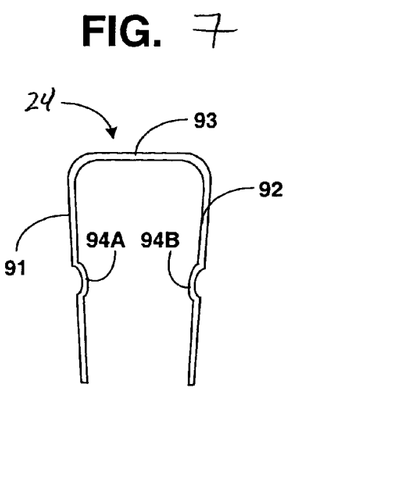
FIG. 7 is a front view of the electrical connector clip of FIG. 5 in a pre-biased or pre-loaded position following full insertion of the connector clip within a portion of a connector block of an implantable medical device.

The components illustrated in FIG. 2 provide a number of advantages. For example, because electrical connector clip 24 is oriented perpendicular to proximal ends 9A and 9B when inserted within channel 21, successive electrical connections can be placed close to one another. In other words, the pitch or "spacing" between adjacent electrodes disposed axially along the lead tip can be reduced, permitting an increased density of electrical interconnections. Accordingly, this feature is particularly useful for in-line lead systems, i.e., systems in which the medical lead includes a number of electrical contacts disposed along axial positions of the lead. In that case, connector block 7 could include a number of connector clip apertures 22 and fluid seal apertures 26 in an alternating configuration. FIGS. 7 and 8 illustrate two such examples and are described below.

Another advantageous feature of connector block 7 according to the present invention is a generally rectangular shaped ridge 29 that is formed within access hole 22. In particular, ridge 29 simplifies insertion of electrical connector clip 24 into hole 22, and facilitates spring biasing of electrical connector clip 24 upon insertion. Ridge 29 tends to bias clip 24 outward to accommodate insertion of proximal end 9A, 9B of leads 2 within clip 24 with reduced insertion force. Additional details of the advantages of one or more ridges are described in detail below with reference to FIGS. 8A and 8B.

In accordance with various embodiments, connector clip aperture 22 and fluid seal aperture 26 may be oriented in any direction along the relevant portion of connector block 7. For example, connector block 7 may be oriented so that apertures 22, 26 are positioned along the top of connector block 7, or along the bottom of connector block 7. In the later case, electrical connector clip 24 would be oriented such that a top contact surface of electrical connector clip 24 faced down for electrical coupling to the circuitry in housing 5.

Figure 3:
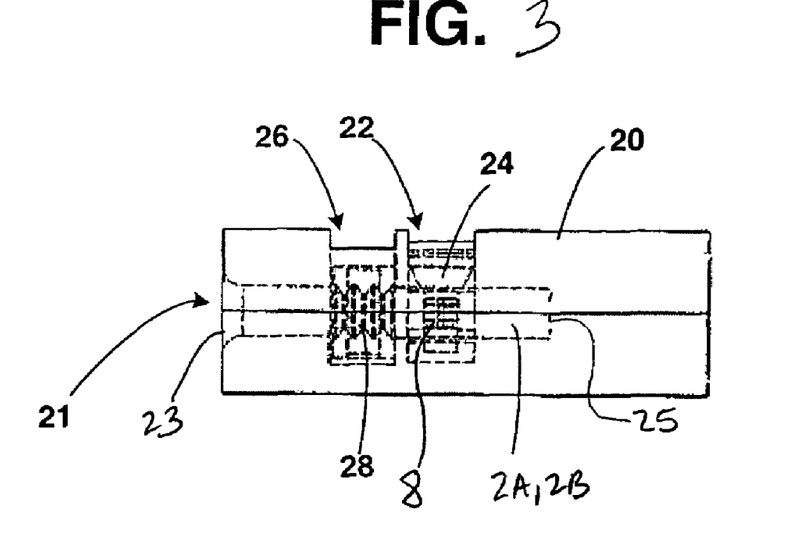
FIG. 3 is a cross-sectional side view of components of a connector assembly of an implantable medical device according to the present invention.
Figure 4:
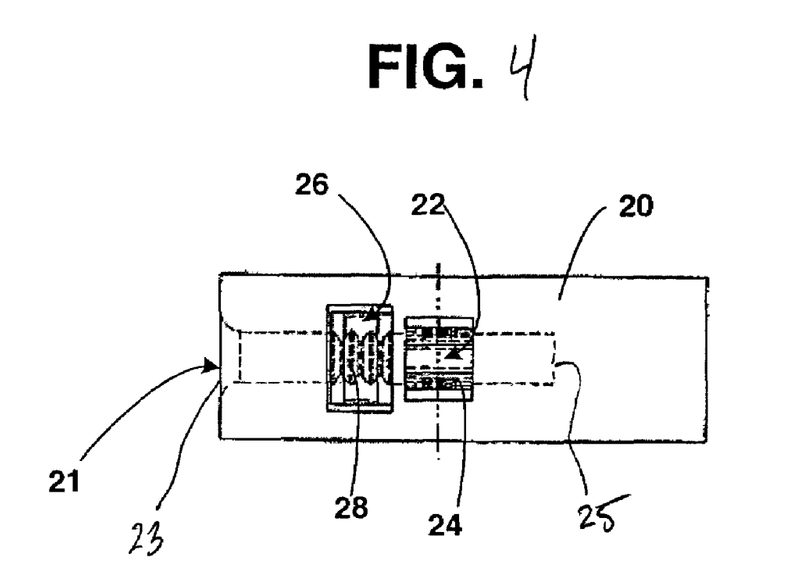
FIG. 4 is a top view of components of the connector assembly of FIG. 3.

FIG. 3 is a cross-sectional side view of components of a connector assembly of an implantable medical device according to the present invention. FIG. 4 is a top view of components of the connector assembly of FIG. 3. As shown in FIGS. 3 and 4, channel 21 is formed through a portion of connector block 7 to define a path for receiving medical lead 2A or 2B. Electrical connector clip 24 is positioned within aperture 22 for electrical coupling to contact areas 8 of one of lead 2A, 2B, and seal 28 is positioned within aperture 26 for sealing leads 2 when inserted within channel 21 of connector block 7. Both connector clip 24 and seal 28 are positioned within connector block 7 so as to be perpendicular to proximal end 9A, 9B of lead 2A or 2B when lead 2A or 2B is inserted within channel 21 of connector block 7 via connector port 20.

Figure 5:
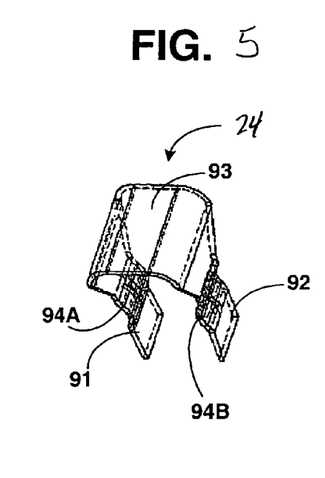
FIG. 5 is a perspective view of an electrical connector clip for coupling a medical lead to circuitry of an implantable medical device according to the present invention.
Figure 6:
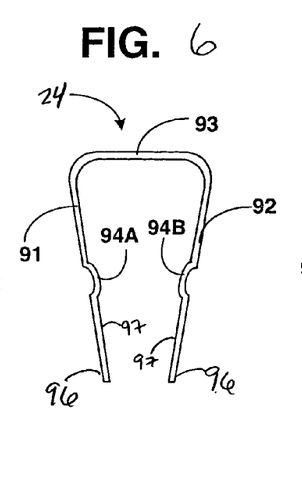
FIG. 6 is a front view of the electrical connector clip of FIG. 5 in a non-biased or preloaded position prior to insertion in a portion of a connector block of an implantable medical device.

FIG. 5 is a perspective view of an electrical connector clip for coupling a medical lead to circuitry of an implantable medical device according to the present invention. FIG. 6 is a front view of the electrical connector clip of FIG. 5 in a non-biased or preloaded position prior to insertion in a portion of a connector block of an implantable medical device, and FIG. 7 is a front view of the electrical connector clip of FIG. 5 in a pre-biased or pre-loaded position following full insertion of the connector clip within a portion of a connector block of an implantable medical device.

As described above, electrical connector clip 24 is used for coupling a medical lead 2A or 2B to circuitry contained within housing 5 of implantable medical device 10. As illustrated in FIGS. 5-7, electrical connector clip 24 includes a first sidewall 91, a second sidewall 92, and an endwall 93 extending between a first end of first sidewall 91 to a first end of second sidewall 92 such that connector clip 24 forms a substantially U-shaped configuration with a second end 95 of first side wall 91 and a second end 96 of second sidewall 92 being spring biased toward one another. Electrical connector 90 may also include protrusions 94A, 94B formed on respective inner surfaces of each of first and second side walls 91, 92. In particular, protrusions 94A, 94B can be formed to facilitate electrical coupling to the medical lead upon positioning of the medical lead within the U-shape of connector clip 24.

Figure 8A:
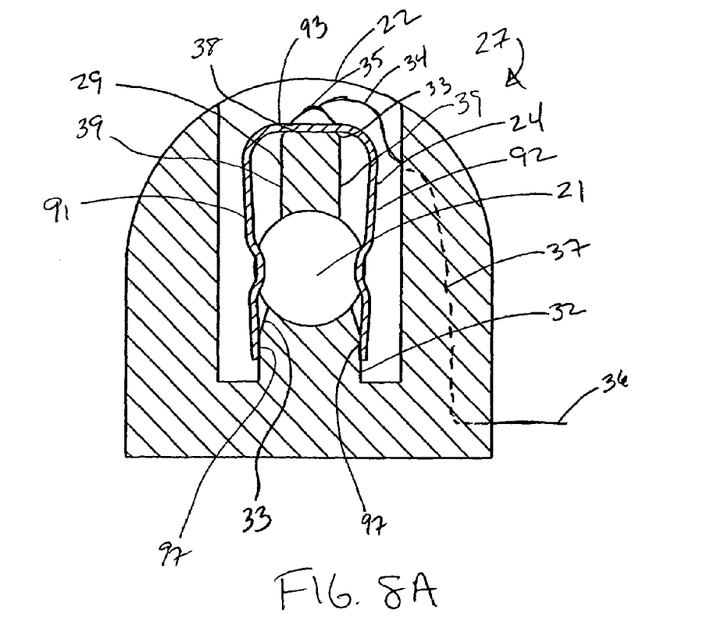
FIG. 8A is a cross-sectional front view of components that form a portion of a connector block of an implantable medical device, according to the present invention, with a connector clip inserted prior to insertion of a medical lead within the connector block.
Figure 8B:
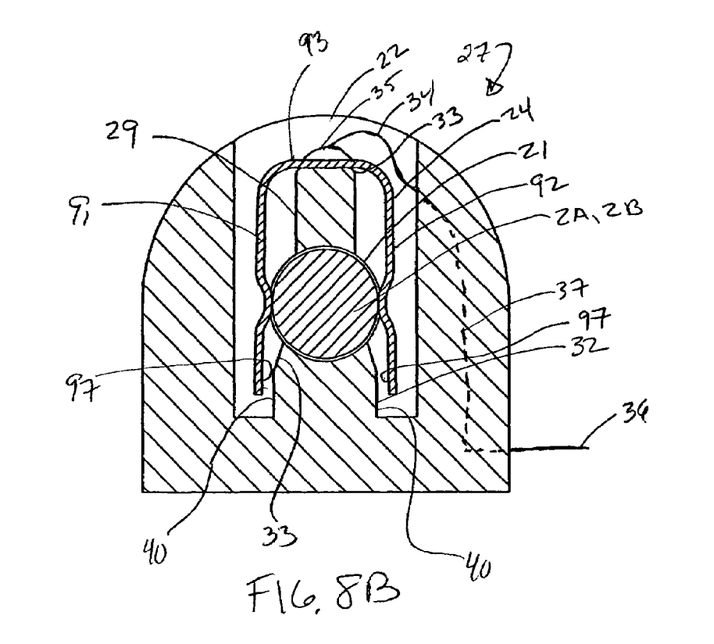
FIG. 8B is a cross-sectional front view of the components of FIG. 8A following insertion of a medical lead within the connector block.

An outer surface of endwall 93 may define a location for welding a wire that couples to circuitry of the IMD (such as illustrated in FIGS. 8A and 8B). Protrusions 94A, 94B each define an electrical coupling surface offset from a major inner surface of the first and second side walls 91, 92. In other words, the surface of protrusions 94A, 94B defines electrical contact points for coupling to a medical lead.

FIG. 8A is a cross-sectional front view of components that form a portion of a connector block of an implantable medical device, according to the present invention, with a connector clip inserted prior to insertion of a medical lead within the connector block. FIG. 8B is a cross-sectional front view of the components of FIG. 8A following insertion of a medical lead within the connector block. As illustrated in FIGS. 8A and 8B, portion 27 of connector block 7 defines channel 21 within which medical lead 2A or 2B is inserted. Electrical connector clip 24 is positioned within aperture 22 and seal 28 is positioned within aperture 26 (not shown in FIGS. 8 and 8B) of portion 27 of connector block 7 prior to insertion of lead 2A or 2B within channel 21, as described above. Upper ridge 29 defines a guide path to simplify insertion of electrical connector clip 24 by directing and spring biasing electrical connector clip 24 when connector clip 24 is inserted within aperture 22. Lower ridge 32 defines a biased position of electrical connector clip 24 prior to insertion of lead 2A or 2B. If desired, lower ridge 32 and/or upper ride 29 can include a slight taper 33 to simplify insertion of electrical connector clip 24 within aperture 22.

This spring bias defined by lower ridge 32 brings electrical connector clip 24 into a spring force range that is desirable for insertion of a lead 2A or 2B into channel 21 (FIG. 2). In other words, ridge 32 functions to bias electrical connector clip 24 into a position in which subsequent insertion of a medical lead into channel 21 causes slight residual spring-forced opening of electrical connector clip 24. This residual spring-forced opening of electrical connector clip 24 may be specifically defined for desired resistance of the insertion of a medical lead into channel 21 while ensuring adequate electrical contact pressure between clip 24 and a corresponding electrode carried by the lead with minimal motion of sidewalls 91, 92 of clip 24. Accordingly, the present invention enables a physician to insert a medical lead within channel 21 with less insertion force and less concern for electrical coupling malfunction.

The use of lower ridge 32 to bias electrical connector clip 24 may also achieve a relatively high electrical contact force between electrical connector clip 24 and an inserted lead, with minimized residual movement of side walls 91, 92 of electrical connector clip 24 upon insertion of the lead. As further illustrated in FIG. 8B, a small gap exists between electrical connector clip 24 and lower ridge 32 following insertion of medical lead 31 because electrical connector clip 24 is biased open by lead 31. Accordingly a good electrical interface between electrical connector clip 24 and lead 31 can be ensured.

In particular, according to the present invention, prior to insertion within portion 27 of connector block 7, connector clip 24 is in the non-biased or preloaded position, as illustrated in FIG. 6. The non-biased connector clip 24 is inserted within aperture 22 so that an upper portion 38 of ridge 29 is advanced between inner walls 97 of sidewalls 91, 92 so that end 95 and end 96 follow side walls 39 of ridge 29 as connector clip 24 is advanced within aperture 22. The distance between ends 95 and 96 of sidewalls 91, 92 is then further increased as ends 95 and 96 are advance along taper 33 of lower ridge 32 and further along side walls 40 of lower ridge 32 until connector clip 24 is fully advanced within aperture 22, with lower ridge 32 placing connector clip 24 in the biased or preloaded position, as illustrated in FIGS. 7 and 8A. As can be seen in FIG. 8A, once connector clip 24 is fully inserted in aperture 22 to be in the biased or pre-loaded position, protrusions of sidewalls 91, 92 project over channel 21 to provide contact points that come in contact with lead 2A or 2B when lead 2A or 2B is inserted within channel 21 and which define electrical contact points for coupling to medical lead 2A or 2B when fully inserted within connector block 7.

As illustrated in FIG. 8B, subsequent advancement of medical lead 2A or 2B within channel 21 causes further residual spring-forced opening of electrical clip 24 so that the distance between ends 95, 96 of respective sidewalls 91, 92 is further increased from the distance between ends 95, 96 when connector clip 24 is in the biased or pre-loaded position of FIGS. 7 and 8A. As a result, ends 95, 96 are no longer in contact with ridge 32, but rather extend outward from side walls 40 of lower ridge 32, transferring all of the spring-force of biased connector clip 24 toward proximal end 9A or 9B of lead 2A or 2B to fixedly position lead 2A or 2B within connector block 7 and ensure electrical contact pressure between connector clip 24 and a corresponding one of contact areas 8.

As illustrated in FIGS. 8A and 8B, end wall 93 of electrical connector clip 24, e.g., the surface connecting the two sidewalls 91, 92 of generally U-shaped electrical connector clip 24, defines a welding surface. Accordingly, an electrical wire 34 can be welded via weld 35 to electrical connector clip 24 to facilitate connection to electrical components of IMD 1. Portion 27 of connector block 7 then defines a conduit 37 through which electrical wire 34 passes. An end 36 of wire 34 is coupled to circuitry of IMD 1. A sealing compound, such as silicone, an epoxy or the like, can then be placed over aperture 22 to seal clip 24 and wire 34 within portion 27 of connector block 7.

Figures 9, 10:
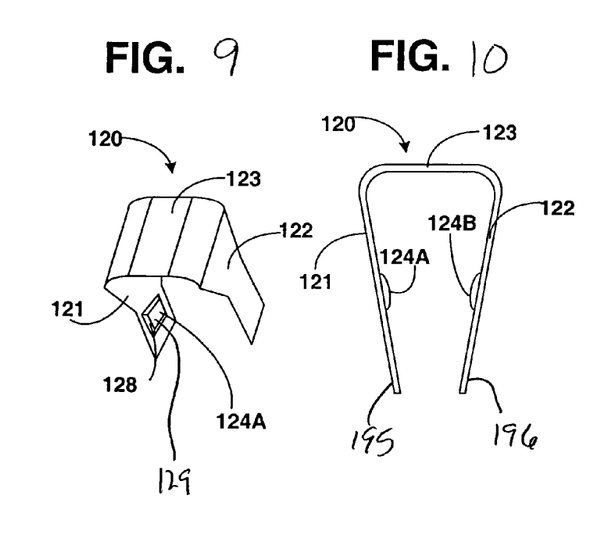
FIG. 9 is a perspective view of an electrical connector clip for coupling an implantable medical lead to circuitry of an implantable medical device according to the present invention.
FIG. 10 is a front view of the electrical connector clip of FIG. 9 prior to insertion within a connector block of an implantable medical device.
Figure 11:
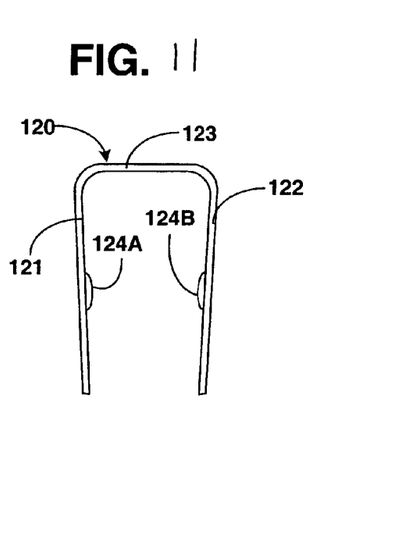
FIG. 11 is a front view of the electrical connector clip of FIG. 9 following insertion within a connector block of an implantable medical device.

FIG. 9 is a perspective view of an electrical connector clip for coupling an implantable medical lead to circuitry of an implantable medical device according to the present invention. FIG. 10 is a front view of the electrical connector clip of FIG. 9 prior to insertion within a connector block of an implantable medical device, and FIG. 11 is a front view of the electrical connector clip of FIG. 9 following insertion within a connector block of an implantable medical device. In particular, FIGS. 9-11 illustrate a slight modification of the electrical connector clip 90 illustrated in FIGS. 5-7, which can further improve insertion of a medical lead.

Like connector clip 24, a connector clip 120 according to an embodiment of the present invention includes a first sidewall 121, a second sidewall 122, and an endwall 123 attaching a first end of first sidewall 121 to a first end of second sidewall 122 such that clip 120 forms a substantially U-shaped configuration with an end 195 of first side wall 121 and an end 196 of second sidewall 122 being spring biased toward one another when connector clip 120 is in a non-biased, preloaded position, illustrated for example in FIG. 10, prior to insertion of connector clip 120 within aperture 22 of portion 27 of connector block 7. Also, electrical connector 120 includes protrusions 124A, 124B formed on inner surfaces of each of first and second side walls 121, which are formed to facilitate electrical coupling to the medical lead upon positioning of the medical lead within the U-shape connector clip 120.

Also similar to connector clip 24, in connector clip 120, an outer surface of endwall 123 defines a location for welding a wire that couples to circuitry of the IMD (such as illustrated in FIGS. 8A and 8B). Protrusions 124A, 124B each define an electrical coupling surface offset from a major inner surface the of the first and second side walls 121, 122.

Unlike connector clip 24, however, protrusions 124A, 124B of clip 120 each define a tapered region 128 between the respective major inner surface of sidewall 121 or 122 and the electrical coupling surface of the respective protrusion 124A or 124B. In particular, region 128 is tapered to facilitate gradual opening of connector clip 120 during insertion of the medical lead through connector clip 120 in a direction perpendicular to connector clip 120. As lead is inserted through connector clip 120, proximal end 9A or 9B comes in contact with and advances within connector clip 120 along tapered region 128 and advances over an upper surface 129 of protrusion 124A and 124B as lead 2 is further advanced through connector clip 120. In this way, tapered region 128 of connector clip 120 improves the functionality of connector clip 120 by reducing the force required for insertion of a medical lead through connector clip 120 and therefore through channel 21 as outlined above. With the inclusion of tapered region 128 on clip 120, a physician can insert the medical lead with greater ease, but the contact force between the lead and electrical contact surfaces of protrusions 124A, 124B after insertion of a lead is unchanged from that of the electrical contact clip illustrated in FIGS. 5-7.

By way of example, first sidewall 121, second sidewall 122 and endwall 123 may be integrally formed of a continuous material. A metal may be used to ensure good conductivity, and a biocompatible metal is generally preferred since the clip 120 forms part of an implantable medical device. Suitable materials for creating clip 120 of FIGS. 12-14 or clip 90 of FIGS. 9-11 may include stainless steals, MP35N, titanium alloys, platinum alloys, or any suitable metal with a correct balance of stiffness, strength, and surface oxided characteristics.

Figure 12:
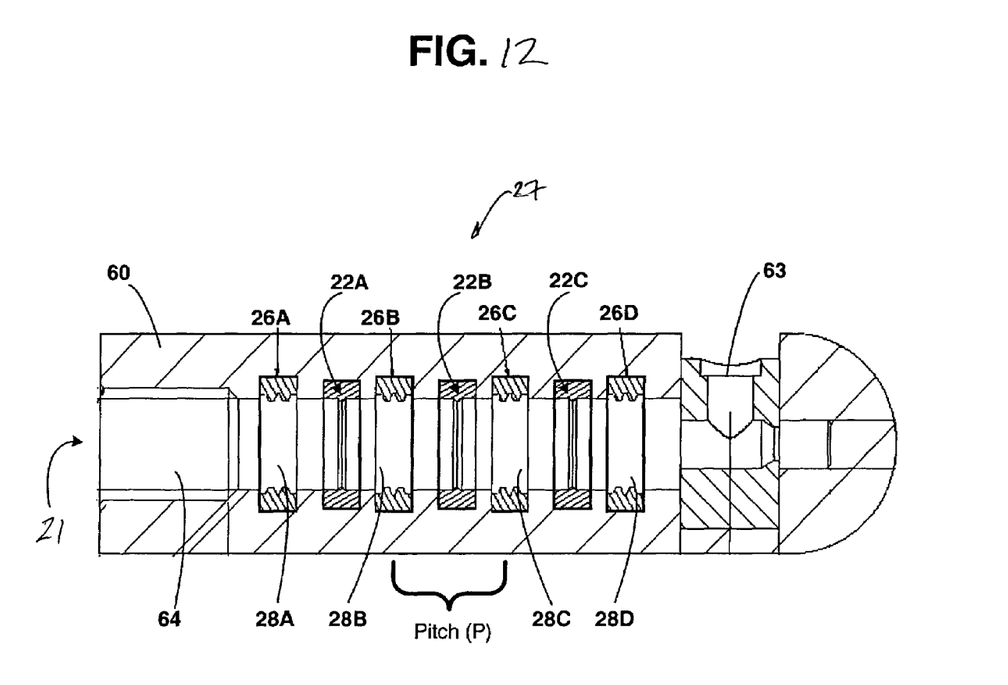
FIG. 12 is a cross-sectional top view of a portion of a connector block of an implantable medical device according to the present invention.

FIG. 12 is a cross-sectional top view of a portion of a connector block of an implantable medical device according to the present invention. As illustrated in FIG. 12, a plurality of connector clip apertures 22A-22C for receiving a plurality of connector clips 24, 120 and a plurality fluid seal apertures 26A-26D for receiving seals 28A-28D can be defined in portion 27 of connector block 7. In particular, apertures 22A-22C for receiving electrical connector clips and apertures 26 for receiving seals are arranged in an alternating configuration so that each respective seal can separate consecutive electrical connector clips inserted into consecutive apertures 22A-22C.

As further illustrated in FIG. 12, portion 27 of connector block 7 is formed to receive a set screw 63. Upon insertion of a medical lead 64 within channel 21 to a desired location, set screw 63 can be inserted to secure medical lead 64 in a final position.

As mentioned above, one advantage of the electrical connector clip described herein is the perpendicular orientation of the electrical connector clip relative to channel 21. Such perpendicular orientation can help reduce the distance between successive electrical contact points of lead 64, which is particularly useful for in-line lead systems. In particular, as illustrated in FIG. 12, use of the described electrical connector clips reduces a pitch (P) to less than approximately 20 millimeters between electrical contacts.

Figure 13:
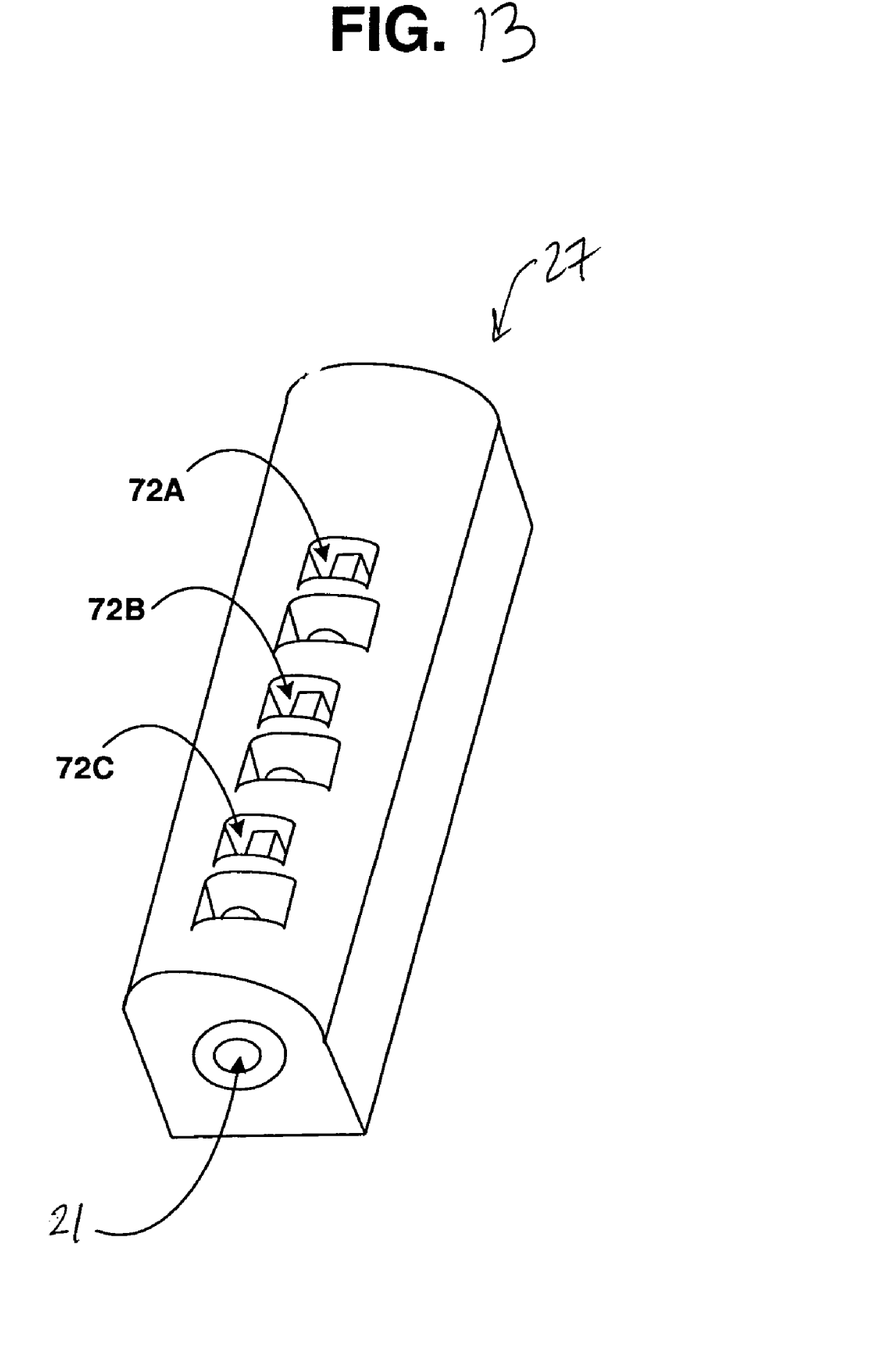
FIGS. 13 and 14 are exemplary perspective views of components of a connector assembly of an implantable medical device according to alternate embodiments of the present invention.
Figure 14:
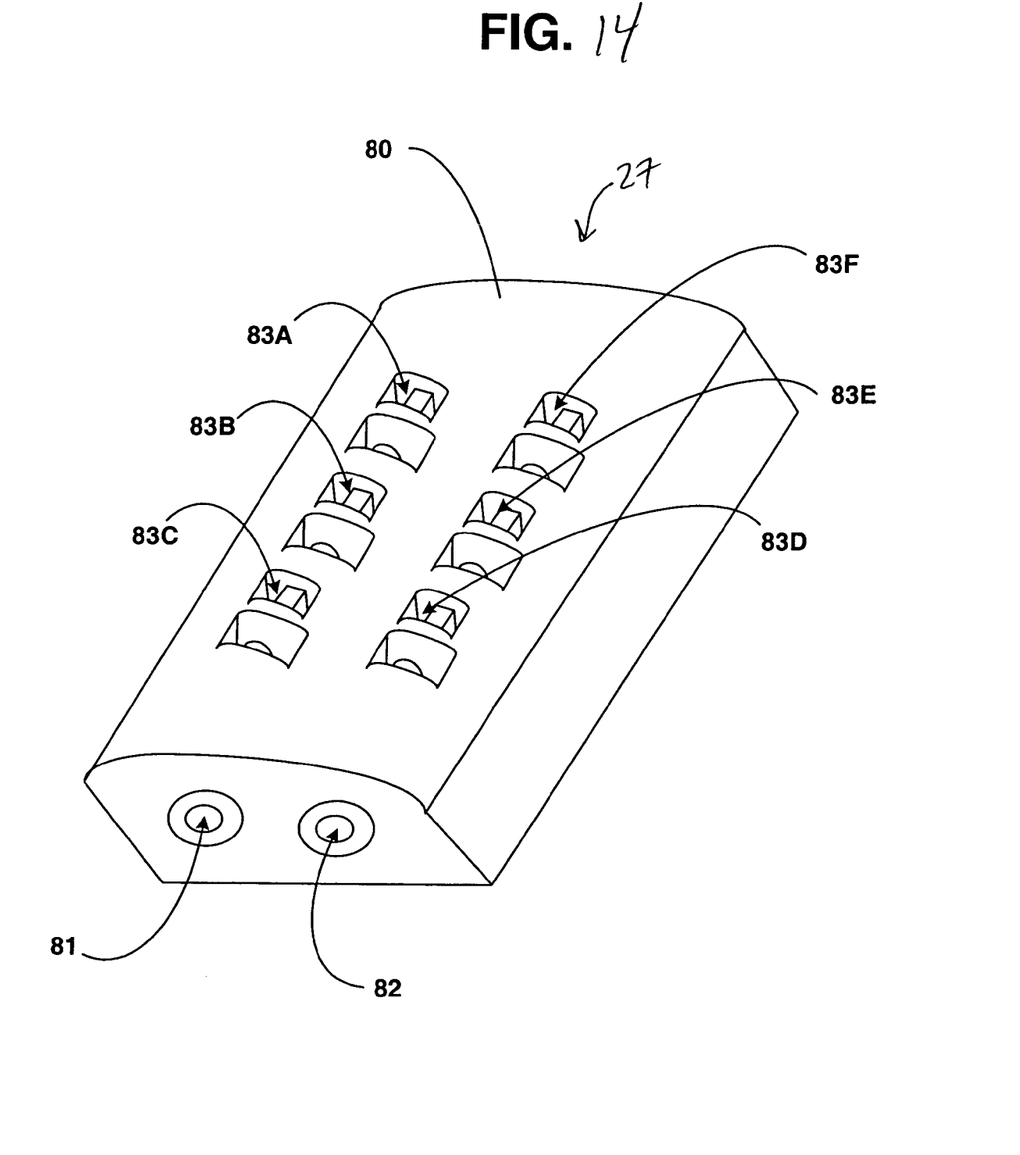

FIGS. 13 and 14 are exemplary perspective views of components of a connector assembly of an implantable medical device according to alternate embodiments of the present invention. In particular, as illustrated in FIG. 13, portion 27 of connector block 7 includes a single row of alternating connector clip apertures 22A-22C for receiving connector clips 24, 120 and fluid seal apertures 26A-26C for receiving seals 28, as described herein. Also, each of apertures 22A-22C include ridge 29 and 32 as described herein to reduce (or possibly increase) insertion force of electrical connector clips into the respective access holes, and to bias the electrical connector clips in order to achieve a desired degree of insertion force for a lead inserted into channel 21.

As illustrated in FIG. 14, portion 27 of connector block 7 may also be formed with a plurality of channels 81, 82 so that more than one lead can be inserted within connector block 7. In the example of FIG. 14, each channel 81, 82 includes a plurality of connector clip apertures 83A-83F, each sized to receive electrical connector clip 24, 120 as described herein to bias the electrical connector clips in order to achieve a desired resistance for insertion of a lead into channel 81.

The present invention improves and simplifies electrical connections between implantable leads and circuitry of an implantable medical device. In particular, the present invention may find useful application in in-line medical lead systems that use leads having multiple electrical contacts along axial positions of the respective leads. In that case, the present invention reduces size constraints of electrical contacts in an IMD, allowing electrical contact areas to be positioned on the lead in closer spatial proximity.

In addition, the present invention improves medical procedures, allowing physicians to make the electrical connections during implantation if the IMD with minimal concern for electrical coupling malfunction. The invention also reduces costs associated with IMD fabrication, which can help minimize patient costs associated with an IMD.

While particular embodiments of the present invention have been shown and described, modifications may be made. It is therefore intended in the appended claims to cover all such changes and modifications, which fall within the true spirit and scope of the invention.

The invention claimed is:

1. A connector assembly for detachably coupling a proximal end of a lead and an implantable medical device, comprising:

a deflectable substantially U-shaped connector clip including a first deflectable arm with a free end, a second deflectable arm with a free end, and a top portion extending between the first arm and the second arm, the first arm and the second arm detachably positioning the proximal end of the lead within the implantable medical device;

a housing portion forming a connector block having a front end with a connector port and having a longitudinal channel extending along a central axis within the housing portion to receive the proximal end of a lead, the connector block further having a connector clip aperture to provide side access to the channel and receive the U-shaped connector clip with the free ends of the arms extending perpendicular to the central axis as the connector clip is positioned within the channel via the connector clip aperture; and a first deflection portion spanning across the connector clip aperture, the first deflection portion fitting between free ends of the first arm and the second arm upon insertion of the connector clip within the connector clip aperture, the first deflection portion causing the connector clip to deflect from a non-biased first position prior to insertion corresponding to a first distance between the first arm and the second arm, upon insertion of the connector clip into the connector clip aperture, to a second position corresponding to a second distance, greater than the first distance, between the first arm and the second arm, wherein the proximal end of the lead further deflects the connector clip from the second position to a third position, corresponding to a third distance between the first arm and the second arm greater than the second distance, the connector clip detachably engaging and electrically coupling the proximal end of the lead to the implantable medical device as the proximal end of the lead is inserted within the channel via the connector port.

2. The connector assembly of claim 1, wherein the first arm and the second arm extend within the channel and are engaged against and electrically couple the proximal end of the lead as the proximal end of the lead is inserted within the channel via the connector port.

3. The connector assembly of claim 1, further comprising a second deflection portion engaging the top portion of the connector clip when the connector clip is in the second position.

4. The connector assembly of claim 3, wherein at least one of the first deflection portion and the second deflection portion includes a tapered portion engaging the connector clip as the connector clip is deflected from the first position to the second position.

5. The connector assembly of claim 1, further comprising a seal member, wherein the housing portion forms a second aperture in fluid communication with the channel, the seal member being insertable within the channel via the second aperture and sealably engaging about the proximal end of the lead as the proximal end of the lead is inserted within the channel via the connector port.

6. The connector assembly of claim 1, wherein the first deflection portion includes a tapered portion engaging the connector clip as the connector clip is deflected from the first position to the second position.

7. The connector assembly of claim 1, further comprising:
   a first flange positioned along the first arm and extending outward toward the second arm; and
   a second flange positioned along the second arm and extending outward toward the first arm, wherein the first flange and the second flange extend within the channel when the connector pin is in the second position.

8. The connector assembly of claim 7, wherein one or both of the first flange and the second flange include a tapered portion to facilitate deflection of the connector clip from the second position to the third position as the proximal end of the lead is inserted within the channel via the connector port.

9. The connector assembly of claim 7, wherein the first deflection portion includes a first side wall and a second side wall, the first arm engaged against the first side wall and the second arm engaged against the second side wall in response to the connector clip being in the second position, and wherein the first arm is spaced from the first side wall, the second arm is spaced from the second side wall, and the first flange and the second flange are engaged against the proximal end of the lead in response to the connector clip being in the third position.

10. The connector assembly of claim 1, wherein the first deflection portion includes a first side wall and a second side wall, the first arm engaged against the first side wall and the second arm engaged against the second side wall in response to the connector clip being in the second position, and wherein the first arm is spaced from the first side wall and the second arm is spaced from the second side wall in response to the connector clip being in the third position.

11. The connector assembly of claim 1, further comprising a protrusion formed along an inner portion of the first arm and the second arm, the protrusion including a tapered portion engaging against the proximal end of the lead as the lead is advanced through the connector clip.

12. The connector assembly of claim 1, wherein the first arm and the second arm are engaged against the first engagement portion when the connector clip is in the second position, and extend outward from the first engagement portion when the connector clip is in the third position.

13. An implantable medical device, comprising:
   a housing portion forming a connector block having a front end with a connector port and having a longitudinal channel extending along a central axis within the housing portion to receive a proximal end of a lead;
   a connector assembly having a deflectable substantially U-shaped connector clip including a first deflectable arm with a free end, a second deflectable arm with a free end, and a top portion extending between the first arm and the second arm, the first arm and the second arm detachably positioning the proximal end of the lead within the implantable medical device;
   the housing connector block further having a connector clip aperture to provide side access to the channel and receive the U-shaped connector clip with the free ends of the arms extending perpendicular to the central axis as the connector clip is positioned within the channel via the connector clip aperture; and
   a first deflection portion spanning across the connector clip aperture, the first deflection portion fitting between free ends of the first arm and the second arm upon insertion of the connector clip within the connector clip aperture, the first deflection portion causing the connector clip to deflect from a non-biased first position prior to insertion corresponding to a first distance between the first arm and the second arm upon insertion of the connector clip into the connector clip aperture, to a second position corresponding to a second distance, greater than the first distance, between the first arm and the second arm, wherein the proximal end of the lead further deflects the connector clip from the second position to a third position, corresponding to a third distance between the first arm and the second arm greater than the second distance, the connector clip detachably engaging and electrically coupling the proximal end of the lead to the implantable medical device as the proximal end of the lead is inserted within the channel via the connector port.

14. The device of claim 13, wherein the first arm and the second arm extend within the channel and are engaged against and electrically couple the proximal end of the lead as the proximal end of the lead is inserted within the channel via the connector port.

15. The device of claim 13, further comprising a second deflection portion engaging the top portion of the connector clip when the connector clip is in the second position.

16. The device of claim 15, wherein at least one of the first deflection portion and the second deflection portion includes a tapered portion engaging the connector clip as the connector clip is deflected from the first position to the second position.

17. The device of claim 13, further comprising a seal member, wherein the housing portion forms a second aperture in fluid communication with the channel, the seal member being insertable within the channel via the second aperture and sealably engaging about the proximal end of the lead as the proximal end of the lead is inserted within the channel via the connector port.

18. The device of claim 13, wherein the first deflection portion includes a tapered portion engaging the connector clip as the connector clip is deflected from the first position to the second position.

19. The device of claim 13, further comprising:
   a first flange positioned along the first arm and extending outward toward the second arm; and
   a second flange positioned along the second arm and extending outward toward the first arm, wherein the first flange and the second flange extend within the channel when the connector pin is in the second position.

20. The device of claim 19, wherein one or both of the first flange and the second flange include a tapered portion to facilitate deflection of the connector clip from the second position to the third position as the proximal end of the lead is inserted within the channel via the connector port.

21. The device of claim 19, wherein the first deflection portion includes a first side wall and a second side wall, the first arm engaged against the first side wall and the second arm engaged against the second side wall in response to the connector clip being in the second position, and wherein the first arm is spaced from the first side wall, the second arm is spaced from the second side wall, and the first flange and the second flange are engaged against the proximal end of the lead in response to the connector clip being in the third position.

22. The device of claim 13, wherein the first deflection portion includes a first side wall and a second side wall, the first arm engaged against the first side wall and the second arm engaged against the second side wall in response to the connector clip being in the second position, and wherein the first arm is spaced from the first side wall and the second arm is spaced from the second side wall in response to the connector clip being in the third position.

23. The device of claim 13, further comprising a protrusion formed along an inner portion of the first arm and the second arm, the protrusion including a tapered portion engaging against the proximal end of the lead as the lead is advanced through the connector clip.

24. The device of claim 13, wherein the first arm and the second arm are engaged against the first engagement portion when the connector clip is in the second position, and extend outward from the first engagement portion when the connector clip is in the third position.

* * * * *